(12) United States Patent
Lin et al.

(10) Patent No.: US 7,632,251 B2
(45) Date of Patent: Dec. 15, 2009

(54) VOLUME ADJUSTABLE, MICRO-INJECTION DEVICE

(75) Inventors: Tsai-Ming Lin, Kaohsiung (TW);
Ping-Sen Liao, Kaohsiung (TW)

(73) Assignee: Dermato-Plastica Beauty (DPB) Co., Ltd., Kaohsiung (TW)

( * ) Notice: Subject to any disclaimer, the term of this patent is extended or adjusted under 35 U.S.C. 154(b) by 196 days.

(21) Appl. No.: 11/808,611

(22) Filed: Jun. 12, 2007

(65) Prior Publication Data

US 2008/0269671 A1    Oct. 30, 2008

(30) Foreign Application Priority Data

Apr. 27, 2007    (TW) .............................. 96114880 A (51) Int. Cl.
    *A61M 5/00*        (2006.01)
(52) U.S. Cl. ................. 604/187; 604/155; 604/218;
        604/233; 604/234; 604/235; 604/246; 604/61;
        604/63; 604/125; 222/144; 222/251; 222/144.5;
        222/167; 222/237; 222/389; 222/390; 433/80
(58) Field of Classification Search ............ 604/61,
        604/63, 125, 218, 233–235, 246; 22/144,
        22/251, 144.5, 167, 237, 333, 389, 390; 433/80–88
    See application file for complete search history.

(56) References Cited

U.S. PATENT DOCUMENTS

| | | | | |
|---|---|---|---|---|
| 1,802,113 A * | 4/1931 | Intemann et al. | ............ | 222/387 |
| 2,269,963 A * | 1/1942 | Wappler | ................ | 604/61 |
| 2,748,767 A * | 6/1956 | Wright | ................ | 604/209 |
| 3,402,712 A * | 9/1968 | Eisenhand | ........... | 604/61 |
| 3,538,916 A * | 11/1970 | Groff et al. | ............ | 604/63 |
| 3,744,493 A * | 7/1973 | Booher et al. | ............ | 604/62 |
| 4,014,331 A * | 3/1977 | Head | ................ | 604/187 |
| 4,067,334 A * | 1/1978 | Haller | ................ | 604/157 |
| 4,105,030 A * | 8/1978 | Kercso | ................ | 604/506 |
| 4,141,467 A * | 2/1979 | Augustijn et al. | ........ | 222/38 |
| 4,403,610 A * | 9/1983 | Lodge et al. | ............ | 604/61 |
| 5,015,233 A * | 5/1991 | McGough et al. | ........ | 604/97.03 |
| 5,024,656 A * | 6/1991 | Gasaway et al. | ........ | 604/70 |
| 5,147,295 A * | 9/1992 | Stewart | ................ | 604/61 |
| 5,172,834 A * | 12/1992 | Wang | ................ | 222/320 |
| 5,228,883 A * | 7/1993 | Blakely et al. | ............ | 604/232 |
| 5,300,029 A * | 4/1994 | Denance | ............ | 604/117 |
| 5,830,194 A * | 11/1998 | Anwar et al. | ............ | 604/223 |
| 6,309,375 B1 * | 10/2001 | Glines et al. | ............ | 604/187 |
| 2004/0122375 A1* | 6/2004 | Woodard et al. | ........ | 604/218 |
| 2005/0261633 A1* | 11/2005 | Khalaj | ................ | 604/181 |

* cited by examiner

*Primary Examiner*—Nicholas D Lucchesi
*Assistant Examiner*—Scott Medway
(74) *Attorney, Agent, or Firm*—Bacon & Thomas, PLLC (57) ABSTRACT

The present invention relates to a volume-adjustable micro-injection device. The device includes a base structure having a syringe positioning structure and a grip, in which the syringe positioning structure can flexibly accommodate injection syringes with different volumes; a holding structure capable of flexibly adjusting an injection angle of syringe content for easier operation; a qualitative controller capable of accurately controlling injection volume; a pressure pushing structure to hold and push a plunger; an injection controller interlinked with the qualitative controller and the pressure pushing structure; and an eject structure facilitating simple operation and easy replacement of injection syringes. In contrast to conventional structures, the present invention provides advantages that control injection volume more accurately, address better injection angle control, allow for the syringe contents to be free from air exposure, require no special syringes, and allow for single-handed replacement of the injection syringe.

18 Claims, 9 Drawing Sheets

VOLUME ADJUSTABLE, MICRO-INJECTION DEVICE

FIELD OF THE INVENTION

The present invention relates to a volume-adjustable micro-injection device capable of being applied to liquid or semi-liquid soft tissue filler transplantation or drug delivery, and more particularly to delivery that can properly, evenly and precisely place a filler or drug into a correct position in the human body. It can be applied to soft tissue augmentation, reconstructive surgery or cosmetic surgery, to achieve low cost, high precision, and simple operation.

BACKGROUND OF THE INVENTION

It has been over one century since fat transplantation/fat grafting was proposed in literature by German doctor, Neüber in 1893 [1]. Fat transplantation/fat grafting has been considered for a long time as a procedure for soft tissue augmentation or filling and thus has been often applied to aspects of reconstructive surgery and cosmetic surgery [2.3].

In general, the side effects of fat transplantation/fat grafting can be one or a combination of absorption, infection, embolism, cyst formation, calcification, ossification, pseudotumor, necrosis, asymmetry, skin necrosis/fistula formation, iatrogenic nerve/vascular injuries, carvenous sinus thrombosis and so forth [4]. After investigation into the causes of said side effects, most are directly related to improper, uneven or excess placement of fat during the fat transplantation/fat grafting procedure. As a result, the correct positioning of fat in a proper, even and precise manner becomes the most critical concern during the clinical application of fat transplantation/fat grafting.

According to the article "Structural Fat Grafting: More Than a Permanent Filler", composed by celebrated plastic surgeon S R Coleman in the well-known journal, Plast. Reconstr. Surg. in 2006, several valuable points [5] pertinent to the correct placement of fat were disclosed. The important points are summarized as follows;

While transplanting fat, the accuracy of the placed volume is extremely important; once the fat is injected into human body, the fat mass can hardly be manipulated again.

When an infiltration cannula is withdrawn each time and the fat is injected spontaneously into the human body during facial fat transplantation, the transplanted fat volume must be precisely controlled down to $1/10$ cc per injection.

The maximum fat injection volume into a specific area of the body, e.g. the eyelid, should be approximately $1/30$ cc or even as low as $1/50$ cc.

Figure 1:
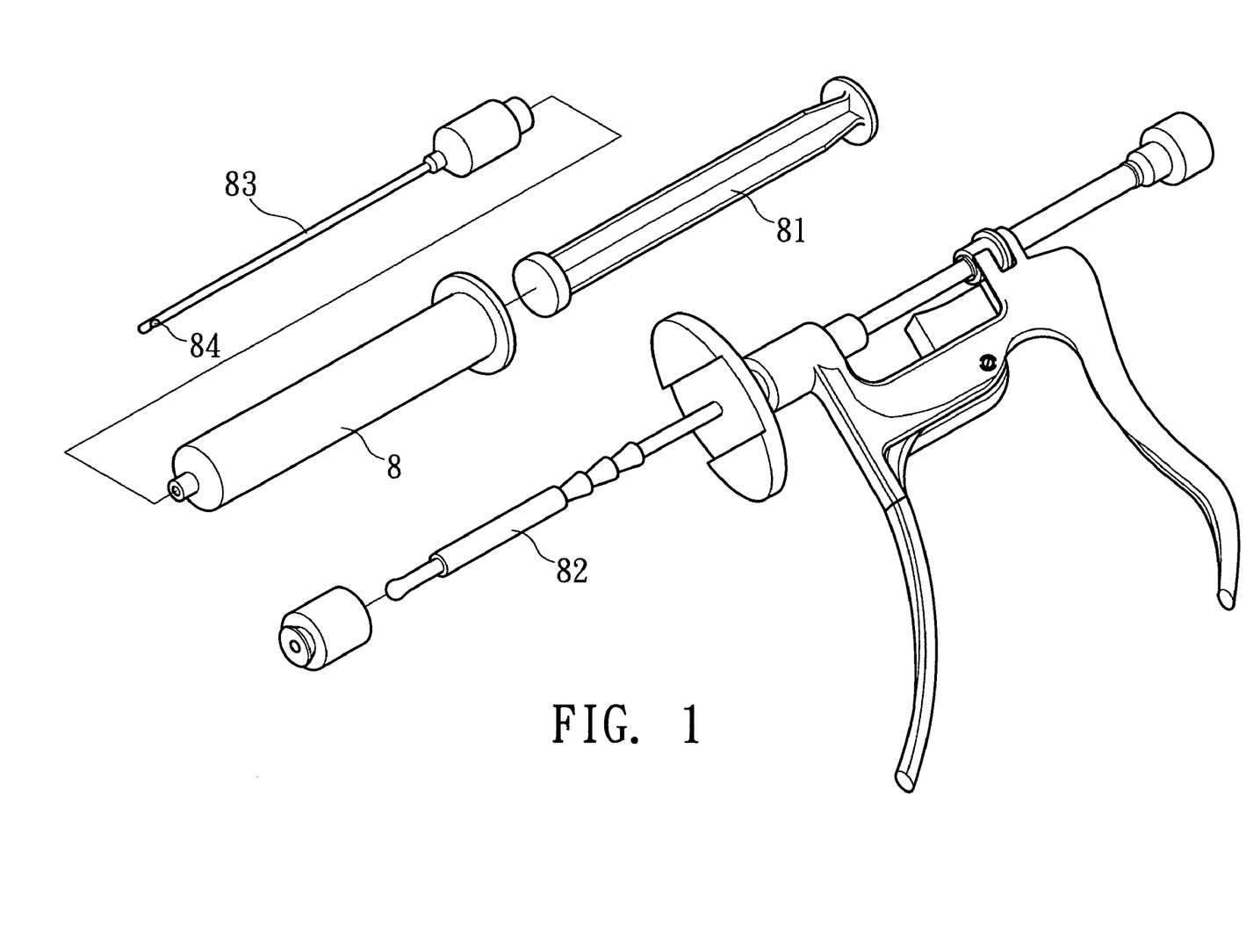
FIG. 1 is an external view of a conventional fat transplantation device.

However, while performing fat transplantation using the 1-cc syringe suggested by S R Coleman during clinical application, a precise advancement of $1/10$ cc of fat per-injection is a very difficult task and, not to mention that an injection volume with an accuracy of $1/30$ or $1/50$ cc is actually beyond human control. For the sake of better surgical effects, the Byron Medical Co. has marketed the DISPOS-A-JECT™ SYSTEM as illustrated in FIG. 1. However, such a system secures a minimum output volume of $1/10$ cc only and obviously fails to achieve the smaller volume demands of $1/30$ or $1/50$ cc. Besides, the 1-cc syringe connected with the DISPOS-A-JECT™ SYSTEM requires a more costly 1-cc BD luer-lock syringe instead of a regular 1-cc syringe supplied in most hospitals and clinics, thus resulting in the deficiency of both operational convenience and universality.

While using the DISPOS-A-JECT™ SYSTEM to perform fat transplantation surgery, as shown in FIG. 1, the plunger 81 of syringe 8 is removed first; then an adapter 82 of the SYSTEM is inserted into syringe 8 to thereby advance the fat. During the operation, the fat is exposed to air and there are concerns that the fat cells may be contaminated and have a low survival rate. Moreover, as the included angle between the gun surface of the SYSTEM and the injection needle 83 and the injection needle aperture 84 is fixed, surgeons do not have flexibility in adjusting the injection angle while the SYSTEM is being clinically applied to fat grafting surgery. As a result, injection surface deviation or injection difficulty easily takes place in the case of a rough operation.

Taking into account the aforementioned descriptions, accuracy of surgery, airtight property of the equipment, simple operation and so on, a novel fat transplantation device is indeed required to resolve these drawbacks arising from the conventional technique.

Notes:
[1] Neüber. Fetttransplantation. Zentrabl. Chir. 22:66, 1893
[2] Chajchir, A., and Benzaquen, I. Fat-grafting injection for soft-tissue augmentation. Plast. Reconstr. Surg. 84:921-24, 1989.
[3] Chajchir, A., Benzaquen, I., Wexler, E., et al. Fat injection. 14:127-36, 1990.
[4] Khawaja, H. A., Handez-perez, E. Fat transfer review: controversies, complications, their prevention, and treatment. Int. J. Cosmet. Surg. Aesth. Dermatol. 4:131-38, 2002.
[5] Coleman, S. R. Structural fat grafting: more than a permanent filler. Plast. Reconstr, Surg. 118:108s-20s, 2006.

SUMMARY OF THE INVENTION

In regards to the first aspect of the present invention, an adjustable micro injection device featuring high accuracy, and easy operation for application to liquid or semi-liquid soft tissue filler transplantation or drug injection is provided. The micro injection device contains a qualitative controller and an injection controller disposed in the base structure. The qualitative controller is employed to precisely control the advancing stroke of the injection controller to control the injection dose of filler or drug. The present invention ensures enhanced surgery accuracy and facilitates operation thereof.

In regards to the second aspect of the present invention, an adjustable micro injection device featuring easy control over an injection direction for application to liquid or semi-liquid soft tissue filler transplantation or drug injection is provided. The micro injection device contains a syringe positioning structure and a holding structure found on the base structure. The syringe positioning structure fastens a syringe, and the holding structure contains a movable angle adjustment knob, having one end for mounting the syringe and the other end for connecting the syringe. By turning the angle adjustment knob, change of the output direction of the filler or the drug inside the syringe is achieved, demonstrating that the present invention provides the function to easily control the injection direction.

In regards to the third aspect of the present invention, an adjustable micro injection device featuring a high airtight property and less expensive cost for application to liquid or semi-liquid soft tissue filler transplantation or drug injection is provided. The micro injection device contains a holding structure at one end of the syringe positioning structure with a pressure pushing structure and an eject structure at the other end. The device can employ a regular syringe commonly seen on the market by virtue of its stabilizing structure to achieve an excellent holding effect without requiring a special syringe that is costly and not commonly available on the market, thereby reducing the cost of injection.

Furthermore, the syringe positioning structure can accommodate syringes with different volumes. Hence, the present invention serves for multiple purposes and can be applied to various surgeries or medical procedures requiring different injection volumes. While replacing the filler or drug, through the design of the eject structure, the overall syringe is directly replaced. As the filler or drug inside the syringe is not exposed to ambient air, the present invention assumes a highly airtight property and lowers the chance of contamination due to contact with external air.

DETAILED DESCRIPTION OF THE PREFERRED EMBODIMENT

The volume-adjustable micro-injection device of the present invention can be applied to liquid or semi-liquid soft tissue filler augmentation or to drug delivery. An injection dose and an injection angle are simply and precisely controlled by a precise injection dose control function and an accurate injection angle adjustment function.

Figure 2:
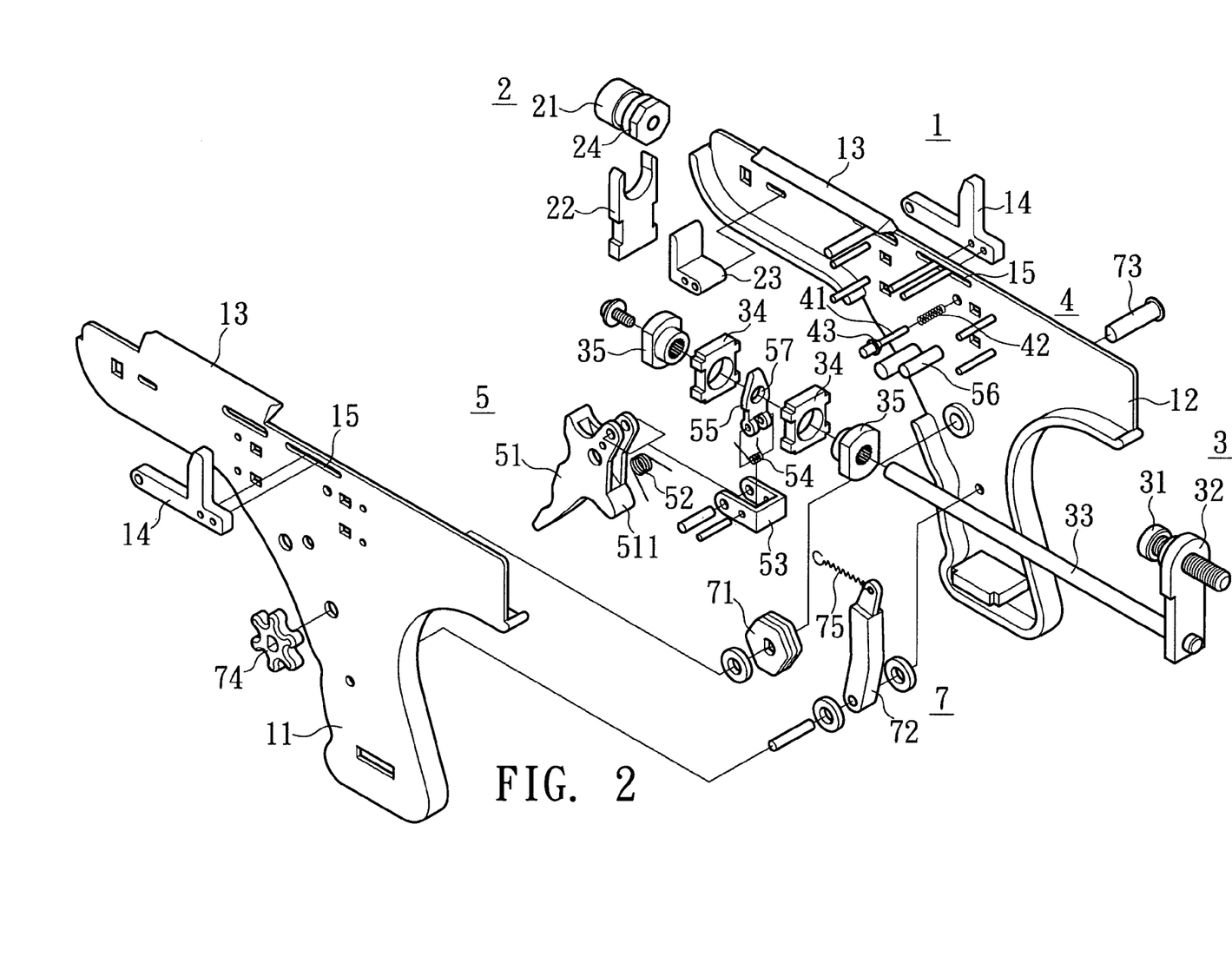
FIG. 2 is an exploded view showing parts of the present invention.
Figure 3:
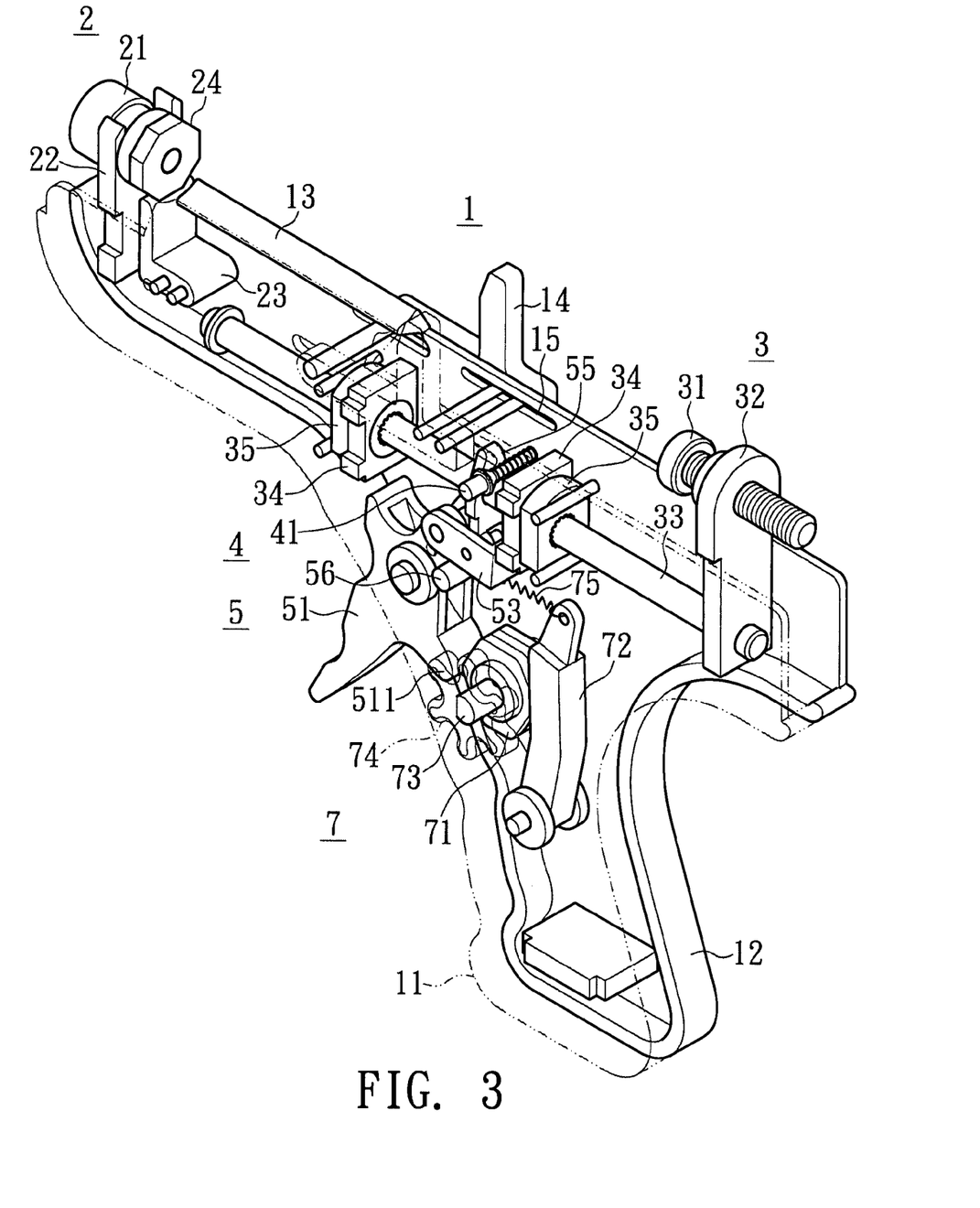
FIG. 3 is a combined external view of the present invention.
Figure 4:
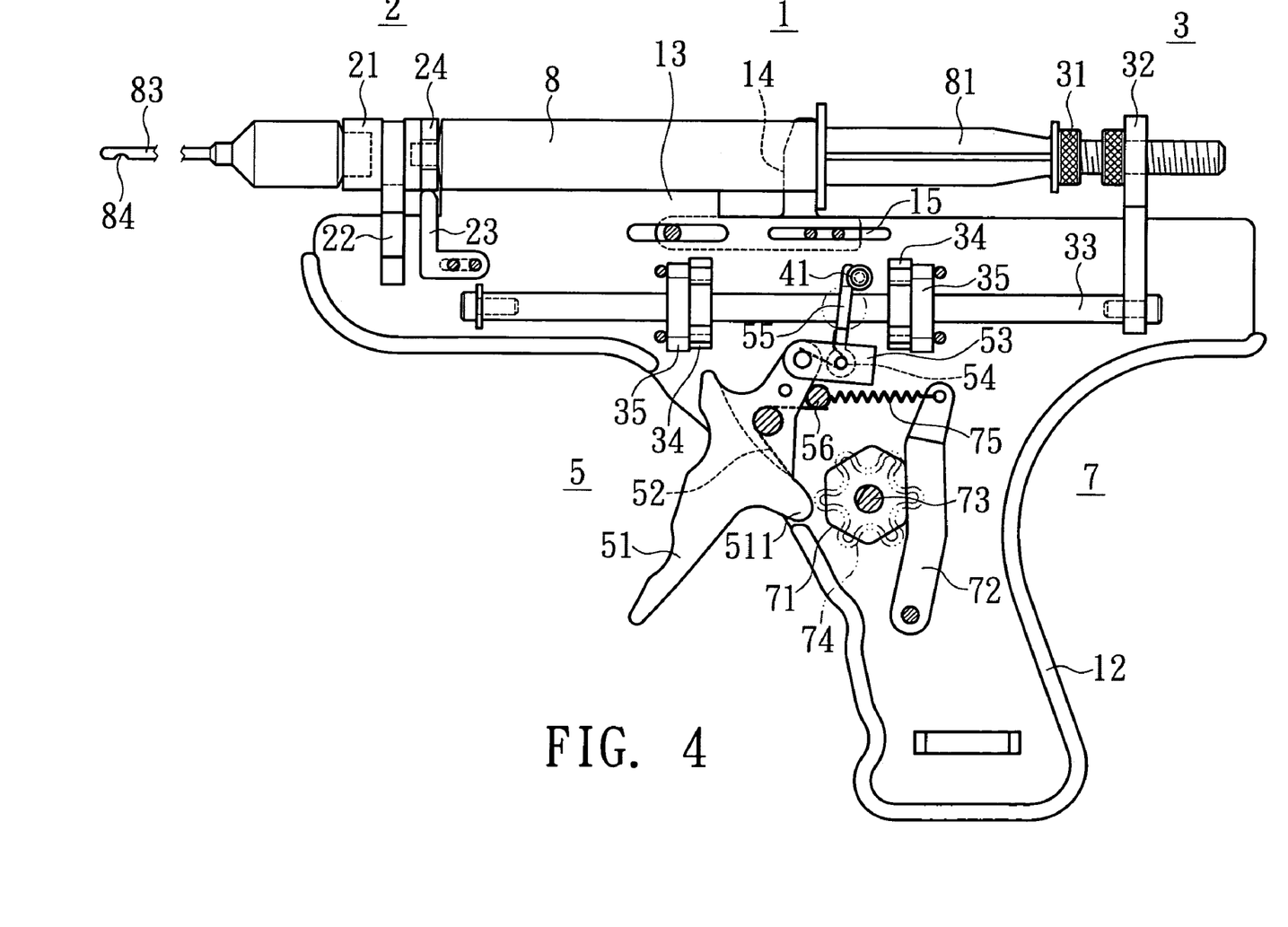
FIG. 4 is a combined plane view of the present invention.

To stand out and fully comprehend the aforementioned objective, features and advantages of the present invention, one preferred embodiment of the present invention is specifically presented along with detailed illustrative descriptions:

In cooperation with the illustration of FIG. 2 and FIG. 3, the preferred embodiment of the present invention pertains to an injection device for liquid or semi-liquid tissue filler transplantation or drug delivery. The device includes a base structure, formed by a left case 11 and a right case 12 and is composed of a metal or non-metal material, e.g. plastic material. The base structure contains a syringe positioning structure 1 for fixing an injection syringe 8 (as shown in FIG. 4) and a grip for the hand to hold and operate the device.

The syringe positioning structure 1 includes a support seat 13 and a syringe positioning block 14. The support seat 13 can either be integrally extended from the left and right cases 11, 12 or individually assembled for forming the position capable of supporting the injection syringe 8. The syringe block 14 is placed in a slide groove 15 on the left and the right cases 11, 12 to allow it to be adjusted and fixed on both sides of the injection syringe 8.

The injection device for liquid or semi-liquid tissue filler augmentation or drug injection in the preferred embodiment of the present invention further includes:

a holding structure 2 located at one end of the syringe positioning structure 1 and at least having an angle adjustment knob 21, a fastener 22 and an angle tenon 23, in which the fastener 22 and the angle tenon 23 are tightly integrated on the base structure. The angle adjustment knob 21 is a movable member and is fitted with the fastener 22 in a tight-fit manner. An injection needle 83 (as shown in FIG. 4) is fitted on one end of the angle adjustment knob 21, and the syringe 8 is successively connected with the other end. The design of the polygonal urging sides 24 of the angle adjustment knob 21 is employed such that after the direction of an aperture 84 of the injection needle 83 is rotationally adjusted, the polygonal urging side is pushed and fixed by the angle tenon 23, the effect of which allows the output direction of the filler or drug inside the injection needle 83 to be adjusted;

a pressure pushing structure 3 containing a push rod adjustment knob 31, a push plate 32, a drive rod 33, two partition plates 34 and two guide blocks 35, in which the two partition plates 34 are tightly integrated in the base structure for fixing the two guide blocks 35 at predetermined positions within the left and the right cases 11, 12 and for penetrating the drive rod 33 through the two guide blocks 35 and reciprocally sliding therebetween. One end of the drive rod 33 is connected with the push rod adjustment knob 31 through the push plate 32, and the push rod adjustment knob 31 is adjusted to push against one end of the plunger 81 of the injection syringe 8;

an eject structure 4 containing an eject tenon 41 and a spring 42, in which the eject tenon 41 has a conical part 43 formed thereon and is movably mounted between the left and the right cases 11, 12 after passing through the spring 42, and is located near the drive rod 33;

an injection controller 5 containing a trigger 51, a return spring 52, a link block 53, a thrust spring 54 and a drive plate 55, wherein the trigger 51 is pivotally positioned between the left and the right cases 11, 12. The link block 53 is used to pivotally connect one end of the trigger 51 and the drive plate 55. The return spring 52 is disposed around the pivot of the trigger 51 (as shown in FIG. 4) for constant urging of one end of the trigger 51 pivotally connected the link block 53 against a fixed column 56. A through hole 57 is provided on the drive plate 55 for the drive rod 33 to pass through, and the thrust spring 54 is mounted to the pivot of the drive plate 55 and the link block 53 for constant urging of a movable end of the drive plate 55 against the eject tenon 41;

a qualitative controller 7 containing a dose control knob 71, a control knob positioning member 72, a synchronous control shaft 73, a knob 74 and a positioning spring 75, in which the dose control knob 71 and the control knob positioning member 72 are all pivotally positioned between the left and the right cases 11, 12. The dose control knob 71 is constituted by a block-like body with unequal sides. A movable end of the control knob positioning member 72 is connected with the above-mentioned fixed column 56 such that the control knob positioning member 72 constantly urges against one of the sides of the dose control knob 71. One end of the synchronous control shaft 73 pivotally mounted to the dose control knob 71 penetrates through the base structure and is fixed with the knob 74 by a forced synchronous coupling selected from the non-circular hole and shaft coupling, key, pin and hub so as to synchronously rotate the knob 74 and the dose control knob 71.

Figure 5:
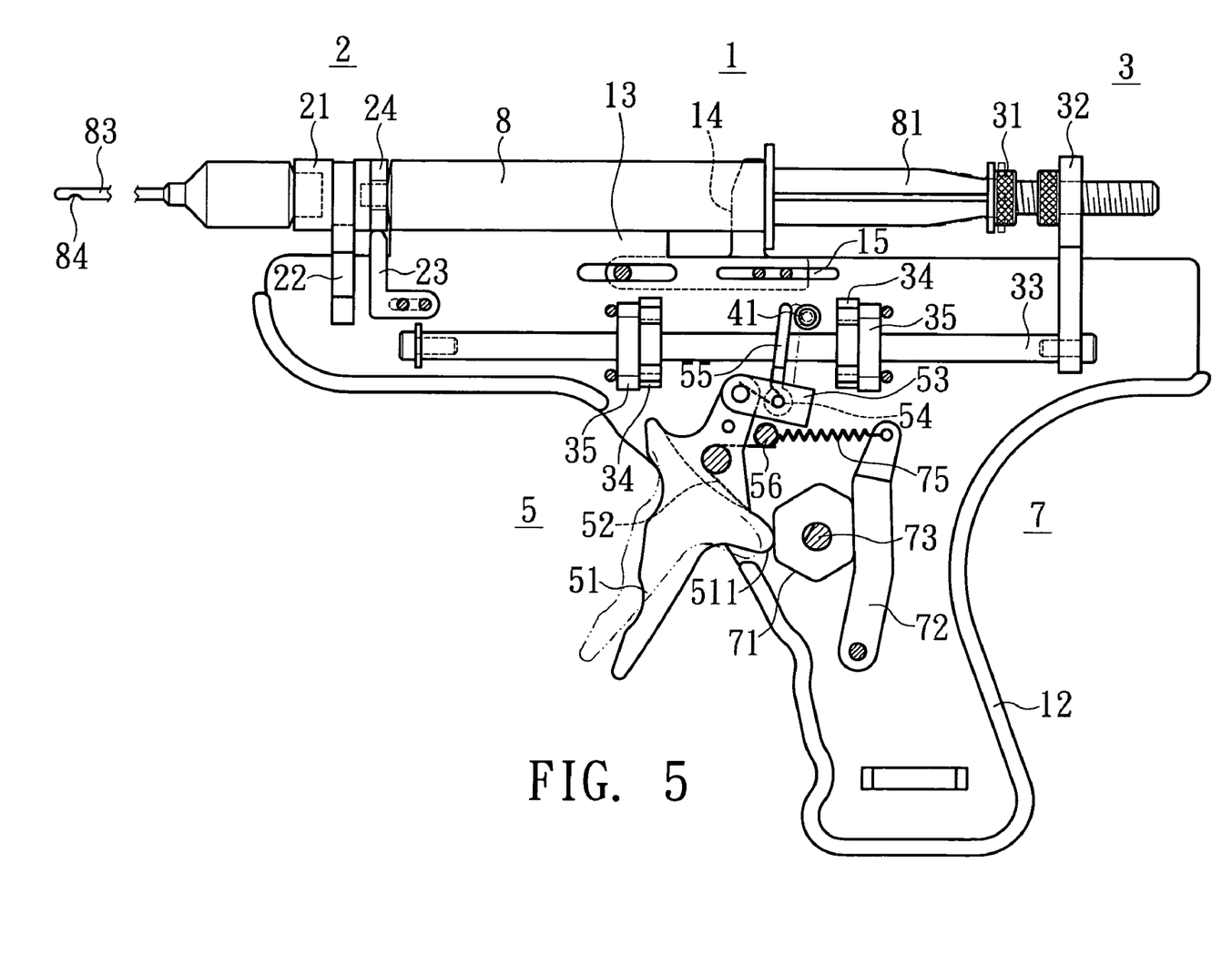
FIG. 5 is an operational movement view showing the injection controller of the present invention.
Figure 6:
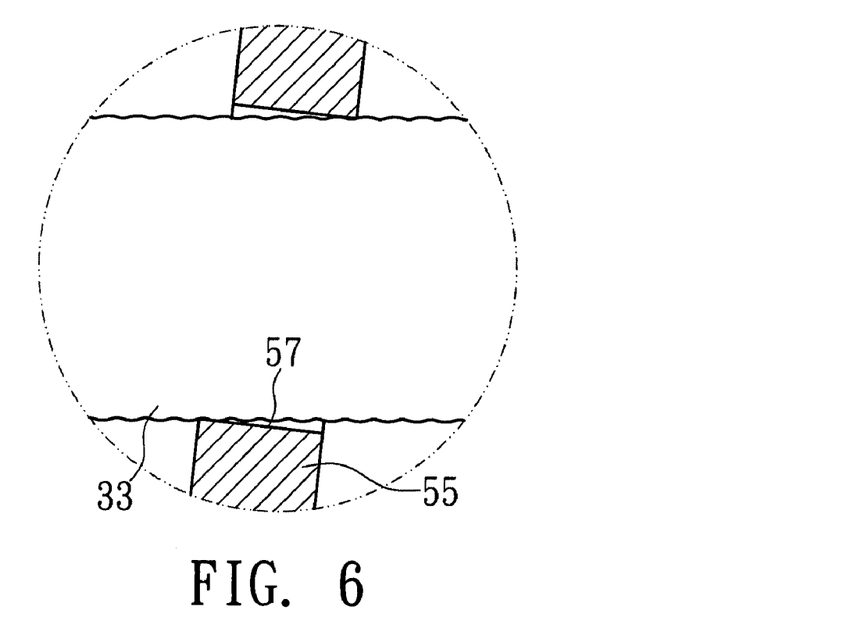
FIG. 6 is an enlarged view showing a partial portion of FIG. 5.

In cooperation with the reference to FIG. 4 and FIG. 5, when pulling the trigger 51, the link block 53 drags the drive plate 55 for synchronous displacement. Together with the illustration of FIG. 6, as the surface of the drive rod 33 has plenty of tiny wavy spiral ripples, the through hole 57 of the drive plate 55 is engaged with the spiral ripples so as to drag the drive rod 33 to synchronously slide. The drive rod 33 drives the push rod adjustment knob 31 to push the plunger 81 of the injection syringe 8 to send out the filler or drug inside the injection syringe 8.

When a protrusion 511 of the trigger 51 urges against one of the sides of the dose control knob 71, the maximum displacement of the trigger 51 is pulled. As such, the pulling angle of the trigger 51 is limited by the dose control knob 71. Meanwhile, the displacement of the plunger 81 pushed by the pressure pushing structure 3 can be constrained accordingly to attain the control effect of the injection dose.

Figure 7:
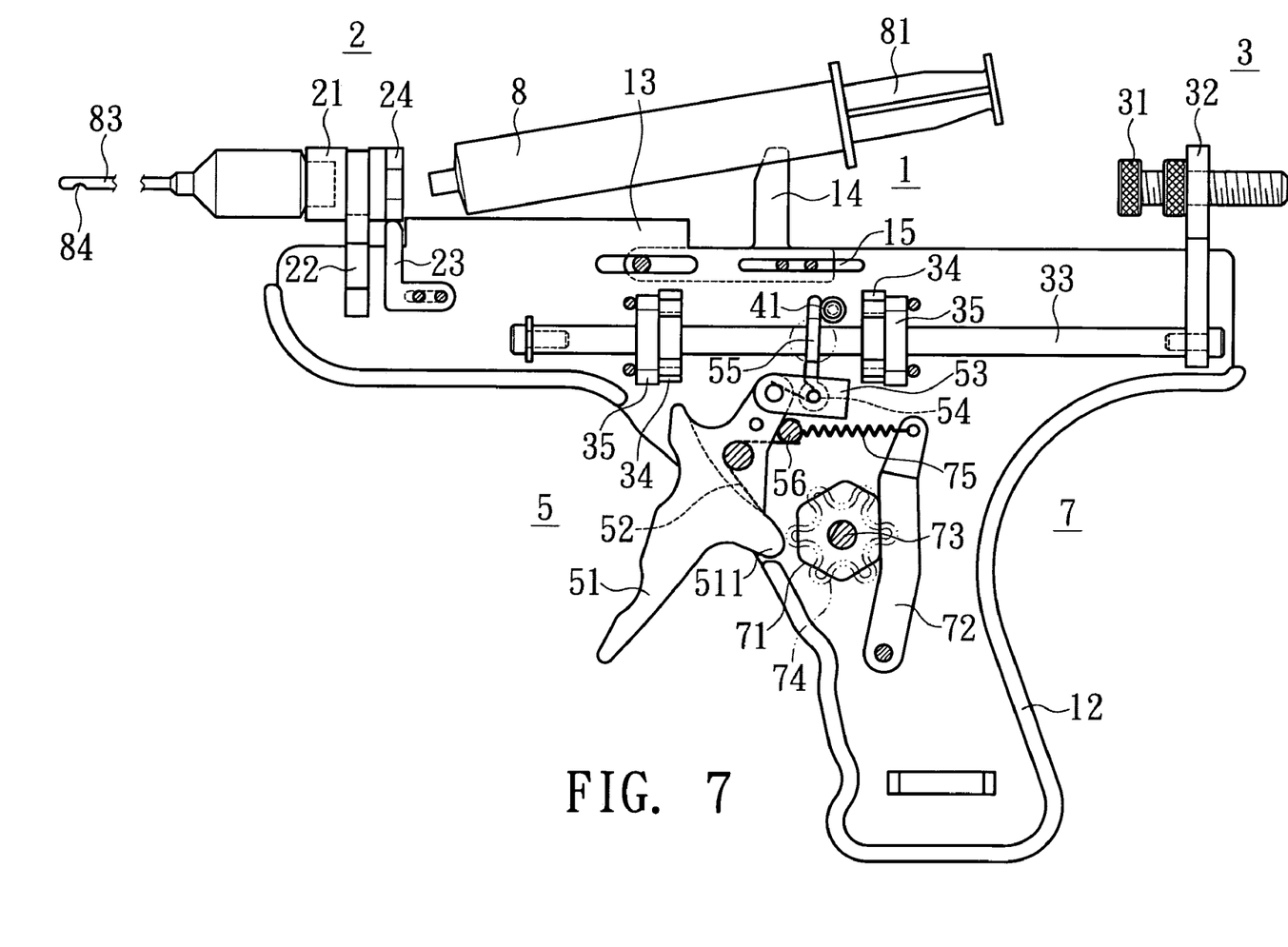
FIG. 7 is an operational movement view showing the eject structure of the present invention.
Figure 8:
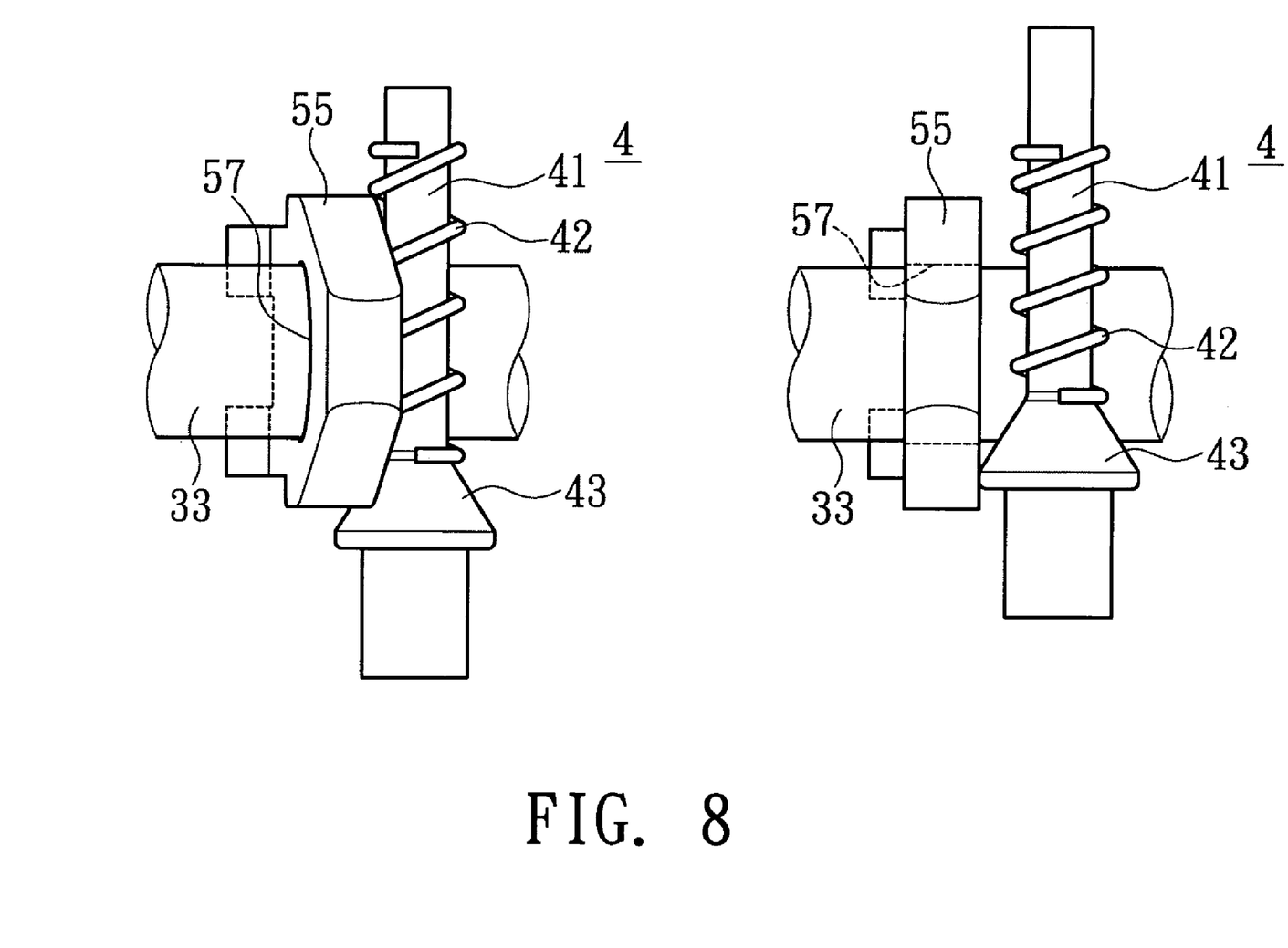
FIG. 8 is a partial movement view showing the eject structure of the present invention.
Figure 9:
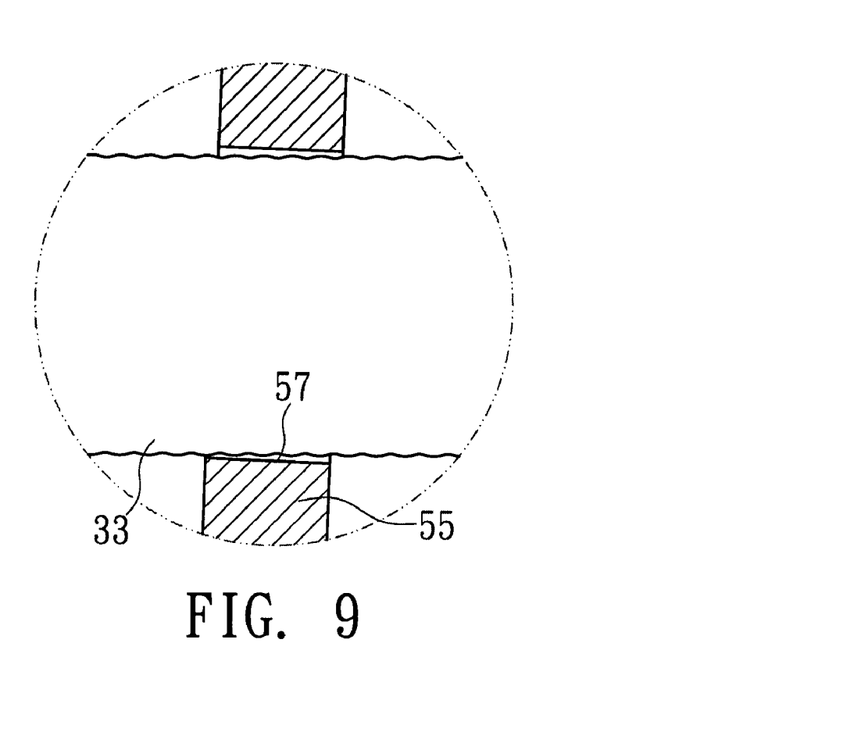
FIG. 9 is an enlarged view showing a partial portion of FIG. 7.

As shown in FIG. 7, when replacing the injection syringe 8, the eject tenon 41 of the eject structure 4 is pushed to axially slide. As shown in FIG. 8, the conical part 43 of the eject tenon 41 pushes the movable end of the drive plate 55 to wobble in an angular orientation. Together with the illustration of FIG. 9, the through hole 57 of the drive plate 55 then disengages from the spiral ripples on the surface of the drive rod 33 such that the pressure pushing structure 3 can be completely pulled out, thereby releasing the injection syringe 8 from a pushing and holding state and facilitating the replacement with another injection syringe 8.

While replacing the injection syringe 8 of the device, the whole structure is replaced. Therefore, the contents inside the injection syringe 8 during the replacement process do not contact with ambient air. As such contamination of the filler or drug inside the syringe is prevented, the bioability of delivered filler or drug is enhanced.

Figure 10:
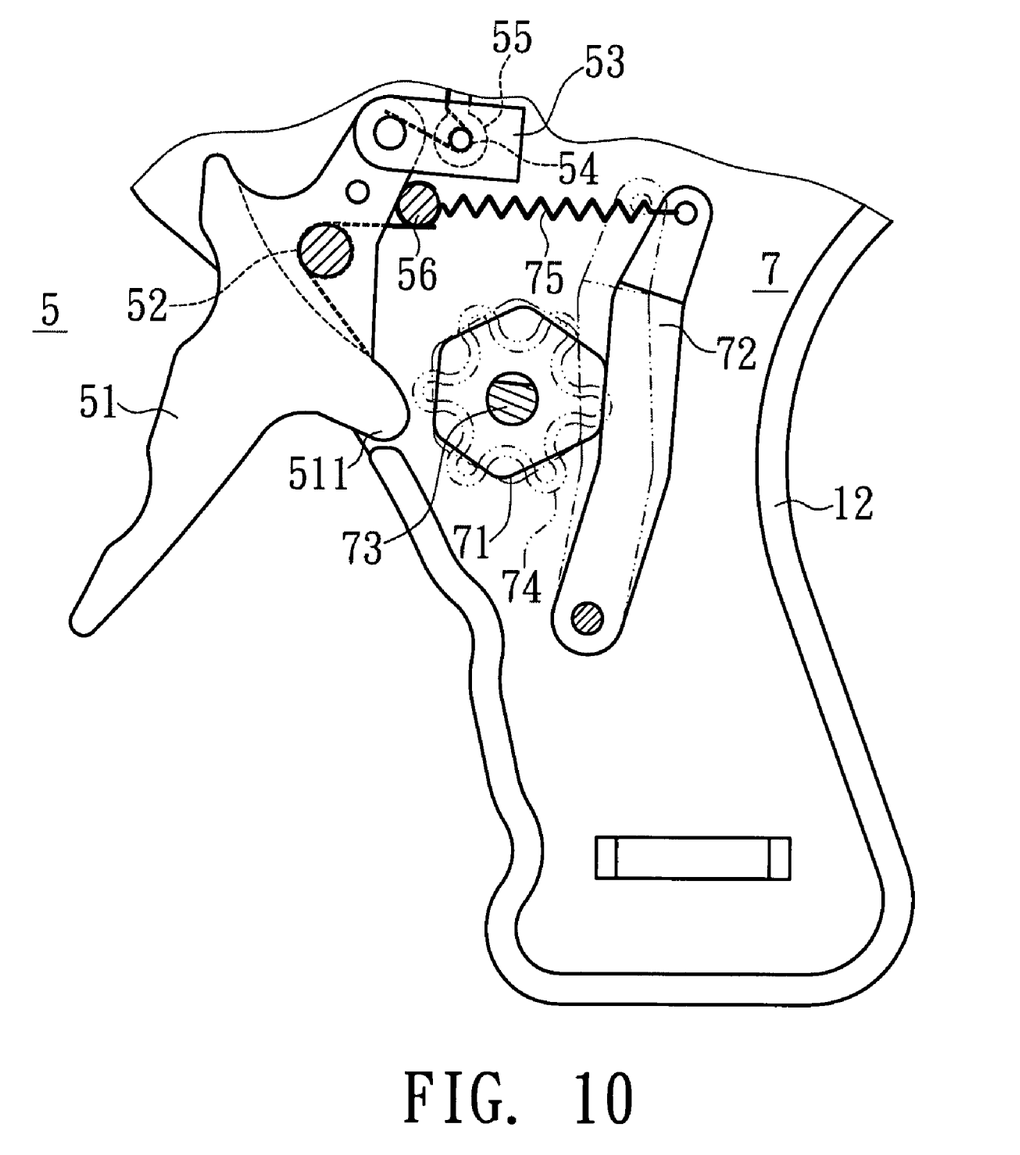
FIG. 10 is an operational movement view showing the qualitative controller of the present invention.

As illustrated in FIG. 10, the device can provide an injection dose control function. The knob 74 is used to select an allowable displacement between the dose control knob 71 and the protrusion 511 of the trigger 51. The control knob positioning member 72 is used to fix a selected side of the dose control knob 71.

In view of different radial distances between each side of the dose control knob 71 and its pivot, the allowable displacement between each side and the protrusion 511 of the trigger 51 is relatively variable as well. The accuracy for a single injection dose can reach ¹⁄₁₀₀ of the maximum volume of the injection syringe. Consequently, the device can provide a multitude of choices for injection doses without the replacement of the injection syringe 8 or the injection device depending on the requirements of injection doses. The present invention provides the advantage that a single system suits for various injection dose demands, the progressiveness in operating convenience and lower cost in contrast to the conventional structure.

In sum, the present invention has better airtight properties, inexpensive cost and completely solves the operational inconvenience and insufficient control accuracy of injection doses arising during surgery. The device of the present invention is extensively applied to fat transplantation in reconstructive and cosmetic surgery, injection of soft tissue fillers (hyaluronic acid, collagen, etc.), delivery of botulinum toxin type-A and other drugs. From the above-mentioned characteristics, these features not only have novel and progressive properties compared to similar products but also have an industrial utility.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be in accordance with the broadest interpretation so as to encompass all such modifications and similar structures.

What is claimed is:

1. A volume-adjustable micro-injection device, comprising:
    a base structure having a syringe positioning structure for receiving an injection syringe and at least a pistol-like grip composed of a left case and a right case for a user's hand to hold and operate;
    a holding structure having an angle adjustment knob, a fastener and an angle tenon located at a first end portion of said syringe positioning structure, wherein the angle adjustment knob has a first end portion for mounting the syringe thereto and a second end portion for connecting an injection needle thereto in a movable manner, and the angle adjustment knob is tightly fitted with the fastener and has a polygonal body with a plurality of urging sides urged and fixed by the angle tenon after a rotational adjustment;
    a pressure pushing structure located at a second end portion of said syringe positioning structure and connected with said base structure;
    an eject structure integrated with said base structure and located in the proximity of said pressure pushing structure;
    an injection controller integrated with said base structure and driving said pressure pushing structure through a drive structure to exert pressure on a plunger of said injection syringe; and
    a qualitative controller including a dose control knob, a control knob positioning member and a positioning spring interlinked with said injection controller to control an allowable displacement of said pressure pushing structure, wherein the control knob positioning member is pivotally disposed in the base structure and a movable end portion thereof is driven by the positioning spring to constantly push against the dose control knob.

2. The device of claim 1, wherein said syringe positioning structure is further comprised of a support seat and a syringe positioning block, said support seat supports said injection syringe, and said syringe positioning block is movably fitted on two sides of said base structure for adjusting and fixing said injection syringe.

3. The device of claim 2, wherein said support seat and said base structure are integrally extended.

4. The device of claim 2, wherein said support seat and said base structure are assembled.

5. The device of claim 2, wherein said base structure has a slide groove on two sides of said base structure respectively for mounting said syringe positioning block.

6. The device of claim 1, wherein said fastener and said angle tenon are tightly fitted with said base structure.

7. The device of claim 1, wherein said pressure pushing structure is further comprised of a push rod adjustment knob, a push plate, a drive rod and two guide blocks; said two guide blocks are tightly coupled to said base structure, said drive rod penetrates through said two guide blocks in a movable manner and is driven by said drive structure of said injection controller, and said push rod adjustment knob is connected with said drive rod through said push plate and is urged against said plunger.

8. The device of claim 7, wherein said drive rod has wavy spiral ripples thereon.

9. The device of claim 7, wherein said pressure pushing structure is further comprised of two partition plates for fixing said two guide blocks at predetermined positions of said base structure.

10. The device of claim 1, wherein said eject structure is further comprised of an eject tenon and a spring; said eject tenon is movably connected in said base structure, and is in contact with said drive structure of said injection controller and has a conical part.

11. The device of claim 8, wherein said injection controller is further comprised of a trigger, a link block and a drive plate; said trigger is pivotally mounted to said base structure, the drive plate is pivotally connected with said trigger through said link block, and said drive plate has a through hole for said drive rod to pass through and drag said drive plate to move.

12. The device of claim 11, wherein said injection controller is further comprised of a return spring and a thrust spring; said return spring is located at a pivot to said trigger such that one end of said trigger is pivotally disposed on said link block and constantly urged against a fixed column of said base structure, and said thrust spring is located at a pivot to said drive plate and said link block such that a movable end of said drive plate is constantly urged against said eject tenon.

13. The device of claim 1, wherein said dose control knob is pivotally disposed at said base structure, said control knob positioning member is urged against said dose control knob, said dose control knob is in the form of a polygonal block-like body having a plurality of unequal sides and different radial distances from any one of said sides to a pivot of said dose control knob so as to limit a turning stroke of said injection controller.

14. The device of claim 13, wherein said qualitative controller is further comprised of a synchronous control shaft and a knob, said synchronous control shaft is pivotally placed in said dose control knob and penetrates through one end of said base structure and is fixed by said knob.

15. The device of claim 14, wherein said synchronous control shaft and said knob are coupled by one forced synchronous coupling selected from a group consisting of a non-circular hole and shaft fitting, key, pin and hub.

16. The device of claim 13, wherein a dose control accuracy of said qualitative controller is in the range of $\frac{1}{10}$ to $\frac{1}{100}$ of a maximum volume of said injection syringe.

17. The device of claim 1, wherein syringe content pertains to fat tissue.

18. The device of claim 1, wherein syringe content pertains to one selected from a group consisting of hyaluronic acid, collagen, botulinum toxin type-A, and liquid and semi-liquid drugs.

* * * * *